(12) United States Patent
Ju

(10) Patent No.: US 10,737,064 B1
(45) Date of Patent: Aug. 11, 2020

(54) BALLOON CATHETER

(71) Applicant: IMEDICOM Co., Ltd., Gunpo-si, Gyeonggi-do (KR)

(72) Inventor: Don Soo Ju, Gunpo-si (KR)

(73) Assignee: IMEDICOM CO., LTD., Gunpo-si, Gyeonggi-do (KR)

( * ) Notice: Subject to any disclaimer, the term of this patent is extended or adjusted under 35 U.S.C. 154(b) by 0 days.

(21) Appl. No.: 16/860,338

(22) Filed: Apr. 28, 2020

(30) Foreign Application Priority Data

Dec. 13, 2019 (KR) ........................ 10-2019-0166557

(51) Int. Cl.
   *A61M 25/01* (2006.01)
   *A61M 25/06* (2006.01)
   *A61M 25/00* (2006.01)
   *A61M 25/09* (2006.01)

(52) U.S. Cl.
   CPC ...... *A61M 25/0136* (2013.01); *A61M 25/007* (2013.01); *A61M 25/0122* (2013.01); *A61M 25/0662* (2013.01); *A61M 2025/0079* (2013.01); *A61M 2025/09008* (2013.01)

(58) Field of Classification Search
   CPC .......... A61M 25/0136; A61M 25/0122; A61M 25/007; A61M 25/0662; A61M 2025/09008; A61M 2025/0079
   See application file for complete search history.

(56) References Cited

U.S. PATENT DOCUMENTS

2005/0272975 A1\* 12/2005 McWeeney ....... A61M 25/0068
                                                                600/113
2010/0312101 A1\* 12/2010 Drontle .................. A61B 17/24
                                                                600/424

FOREIGN PATENT DOCUMENTS

KR    10-2018-0113660 A    10/2018

\* cited by examiner

*Primary Examiner* — Amber R Stiles
(74) *Attorney, Agent, or Firm* — Rabin & Berdo, P.C.

(57) ABSTRACT

A balloon catheter is provided, which includes a balloon guide tube, a balloon moving part, and a bending adjustment part for bending an end of the balloon guide tube, wherein the bending adjustment part includes first and second wires of which one ends are fixed to a ring part, respectively, and a steering handle to which the other ends of the first and second wires are fixed, the central portion of the steering handle is positioned on an extension line from a center line of the balloon guide tube, the other ends of the first and second wires are respectively inserted into wire guide holes of the steering handle formed at a same distance from the central portion of the steering handle, and a plane formed by the first and second wires is perpendicular to the central portion of the steering handle.

10 Claims, 14 Drawing Sheets

BALLOON CATHETER

CROSS-REFERENCE TO RELATED APPLICATIONS

This application claims priority from Korean Patent Application No. 10-2019-0166557, filed on Dec. 13, 2019 in the Korean Intellectual Property Office, the disclosure of which is incorporated herein by reference in its entirety.

BACKGROUND

Technical Field

The present disclosure relates to a balloon catheter.

Background Art

Human body has certain hollow cavities in the facial bones, and these hollow spaces are called the sinuses. In addition, sinusitis refers to the inflammation caused by bacteria or viruses penetrating into these hollow spaces or sinuses.

A balloon catheter is used as a method for treating sinusitis, and this method has an advantage of faster recovery after procedure when compared to the conventional surgical method.

The sinusitis procedure using the balloon catheter is performed by, first, inserting a catheter into the nasal cavity, and then inflating the balloon positioned at the end of the catheter at the entrance of the sinus, and removing inflammation, secretions, and the like inside the sinus.

FIG. 13 shows a balloon catheter that can be used for sinusitis surgery disclosed in Korean Patent Publication No. 10-2018-0113660. For reference, FIG. 13 corresponds to FIG. 1 of the Korean Patent Publication No. 10-2018-0113660 mentioned above, and reference numerals and the like are indicated as they are without modification for convenience.

Meanwhile, the balloon catheter described above has a problem in that it is difficult to insert the balloon catheter to an appropriate position in the sinus, as it is not possible to bend an end of the balloon catheter at a desired angle and fix the same at the bent angle in an on-off manner.

SUMMARY

The present disclosure has been made to overcome the problems mentioned above, and it is an object of the present disclosure to provide a balloon catheter which enables an operator to bend an end of the catheter by an angle desired by the operator to a desired position and then fix the same in an on-off manner.

In an aspect of the present disclosure, there is provided a balloon catheter, which may include a body portion comprising an upper cover and a lower cover, a balloon guide tube, a balloon moving part for slidably moving the balloon along the balloon guide tube, and a bending adjustment part for bending an end of the balloon guide tube. The bending adjustment part may include a ring part fixedly enclosed in the end of the balloon guide tube, first and second wires of which one ends are fixed to the ring part, respectively, and a steering handle to which the other ends of the first and second wires are fixed. The steering handle may be rotatable clockwise or counterclockwise with respect to its central portion. The central portion of the steering handle may be positioned on an extension line from a center line of the balloon guide tube. The other ends of the first and second wires may be respectively inserted into wire guide holes of the steering handle formed at a same distance from the central portion of the steering handle. A plane formed by the first and second wires may be perpendicular to the central portion of the steering handle.

In addition, the upper cover may include a steering handle through hole through which a steering handle body of the steering handle is protruded, and a wall portion extending from a periphery of the steering handle through hole to an interior of the upper cover. A flange of the steering handle may be caught by the wall portion so that the steering handle does not detach from the upper cover.

In addition, a rotation stopper for stopping a rotation of the steering handle may be further provided. The rotation stopper may include a bar passed through the upper cover and the lower cover, a bar flange portion extending from the bar, a locking jaw extending from the bar flange portion and selectively engaged with a plurality of locking grooves of the steering handle, and an elastic member of which one end is in contact with the bar flange portion and the other end is in contact with an inner wall of the lower cover.

In addition, the balloon moving part may include a tube pipe enclosing the balloon guide tube therein and relatively slidable along the balloon guide tube, and having the balloon fixed at one end, and a tube pipe moving part fixed to the tube pipe and moving the tube pipe in a direction in which the balloon guide tube is extended and in a direction opposite to the direction.

In addition, the tube pipe may be coated with the same material as the balloon, and the balloon may be fused to the tube pipe.

In addition, the balloon guide tube may include three through holes formed therein, and the first and second wires may be passed through two of these through holes, respectively, and a LED fiber may be passed through the other through holes that is positioned at a center of the balloon guide tube.

In addition, the body portion may include a power supply that supplies power to the LED fiber, and a blocking plate that is inserted into a slit of the upper cover to selectively block the power supply from the power supply to the LED fiber.

In addition, a fluid port capable of supplying fluid to the balloon may be further provided, in which a fluid supply tube extending from the fluid port may surround the tube pipe and be connected to a fluid supply tube fixing pipe fixed to an outer wall of the tube pipe, a fluid inflow hole may be formed in the outer wall of the tube pipe, through which the fluid discharged from the fluid supply tube may be introduced, and the fluid may be sequentially introduced into the fluid port, the fluid supply tube, and the fluid inflow hole, and supplied to the balloon through a flow path between an inner wall of the tube pipe and an outer wall of the balloon guide tube.

In addition, on a lower surface of the steering handle, fixing parts may be positioned at a same distance from a central portion of the steering handle, and the other ends of the first and second wires may be respectively wound around the fixing parts.

In addition, a protrusion may be provided on a flange of the steering handle, in which the protrusion may be sequentially inserted into and separated from a plurality of grooves formed on a bottom surface of the wall portion of the upper cover when the steering handle is rotated.

In addition, the balloon moving part may be interlocked and moved integrally with the tube pipe and the fluid supply tube fixing pipe.

The balloon catheter according to the embodiment of the present disclosure having the configuration described above has the following effects.

Since the other ends of the first and second wires are respectively inserted into the wire guide holes of the steering handles formed at the same distance from the central portion of the steering handle, and the plane formed by the first and second wires is perpendicular to the central portion of the steering handle, when the steering handle is rotated, the ends of the balloon guide tube are bent on the plane formed by the first and second wires, so that the operator can accurately adjust the bending direction of the end of the guide tube. In addition, the central portion of the steering handle is positioned on the extension line from the center line of the balloon guide tube, so that the operator can easily adjust the degree of bending of the end of the balloon guide tube.

The protrusion is sequentially inserted into and separated from the plurality of grooves formed on the bottom surface of the wall portion of the upper cover when the steering handle is rotated, so that the operator can intuitively estimate the rotation angle of the steering handle.

The outer surface of the tube pipe is first coated with the same material as the balloon, and then the balloon is fused to the tube pipe, so that, when the balloon is inflated, it is possible to reliably prevent fluid from leaking out of the balloon.

The steering handle can be easily prevented from rotating in an on-off manner by using the rotation stopper, so that the end of the catheter can be fixed and unfixed at the bent angle.

Meanwhile, although the present disclosure is not explicitly described, it also includes other effects that can be expected from the configuration described above.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION

Hereinafter, preferred embodiments of the present disclosure will be described in detail with reference to the accompanying drawings, that will be readily apparent to those skilled in the art to which the present disclosure pertains. However, the description proposed herein is just a preferable example for the purpose of illustrations only, and not intended to limit the scope of the disclosure, so it should be understood that other equivalents and modifications could be made thereto without departing from the scope of the disclosure.

Figure 1A:
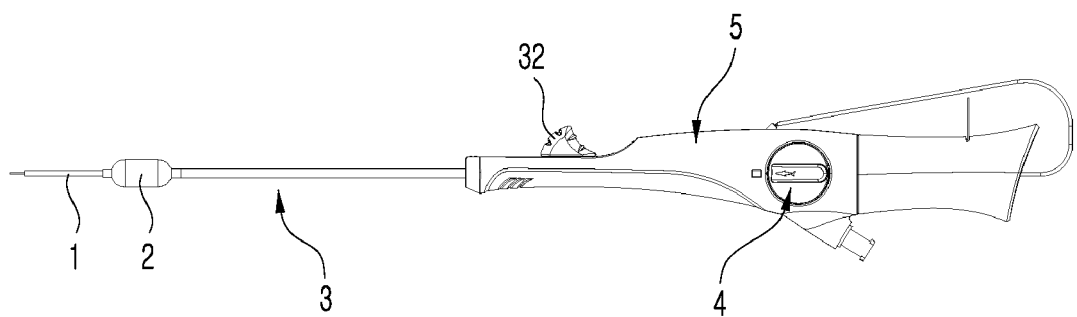
FIG. 1A is a plan view of a balloon catheter according to an embodiment of the present disclosure.
Figure 1B:
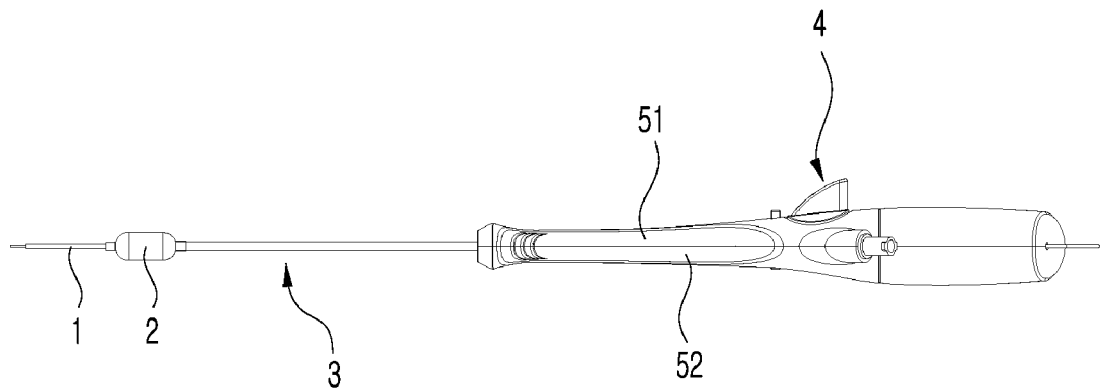
FIG. 1B is a side view thereof.
Figure 1C:
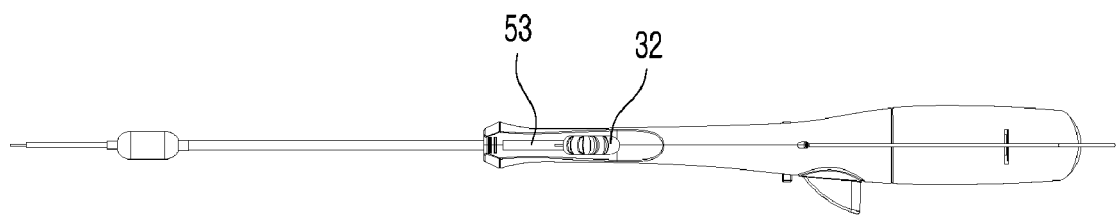
FIG. 1C is a side view thereof viewed from another side.

FIGS. 1A to 1C are schematic diagrams of a balloon catheter according to an embodiment of the present disclosure.

The balloon catheter according to an embodiment includes a body portion 5 including an upper cover 51 and a lower cover 52, a balloon guide tube 1, a balloon moving part 3 for slidably moving a balloon 2 along a balloon guide tube 1, and a bending adjustment part 4 for bending an end of the balloon guide tube 1.

Figure 2:
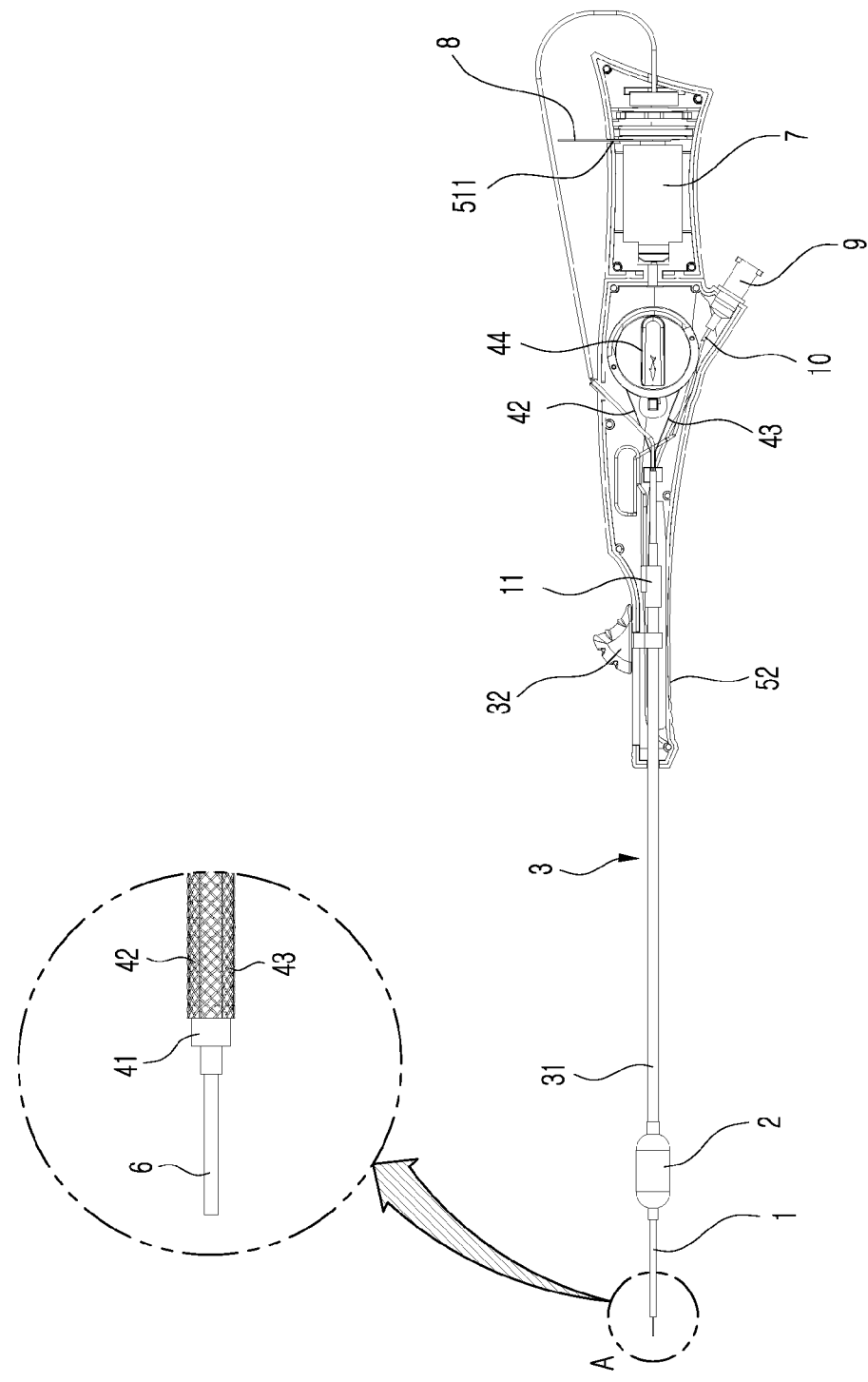
FIG. 2 is a main configuration view showing the balloon catheter of FIGS. 1A to 1C from which an upper cover is removed.

As shown in FIG. 2, the bending adjustment part 4 includes a ring part 41 fixedly enclosed in an end of the balloon guide tube 1, and first and second wires 42, 43 having one ends fixed to the ring part 41, respectively, and a steering handle 44 to which the other ends of the first and second wires 42, 43 are fixed.

The balloon guide tube 1 includes braided wire, which makes the balloon guide tube 1 a flexible tube having rigidity of the tube. The balloon guide tube 1 may additionally include an additional tube 2 which secondly wraps around the braided wire.

Figure 3:
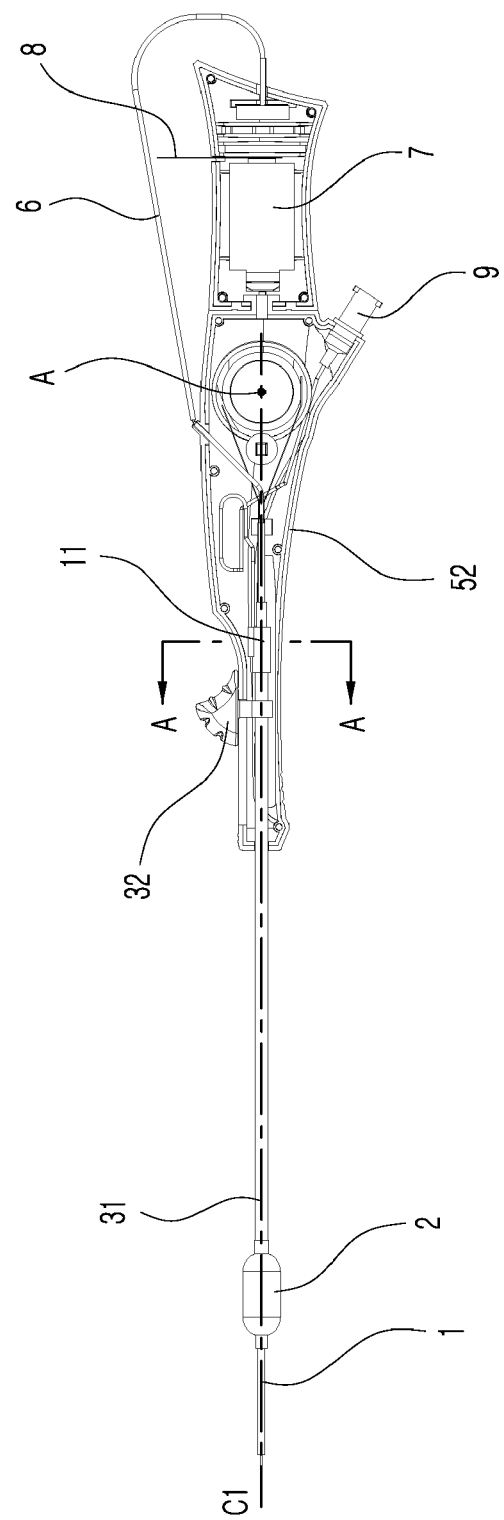
FIG. 3 shows the balloon catheter of FIGS. 1A to 1C in which a central portion of a steering handle is positioned on an extension line of a center line of the balloon guide tube.
Figure 4:
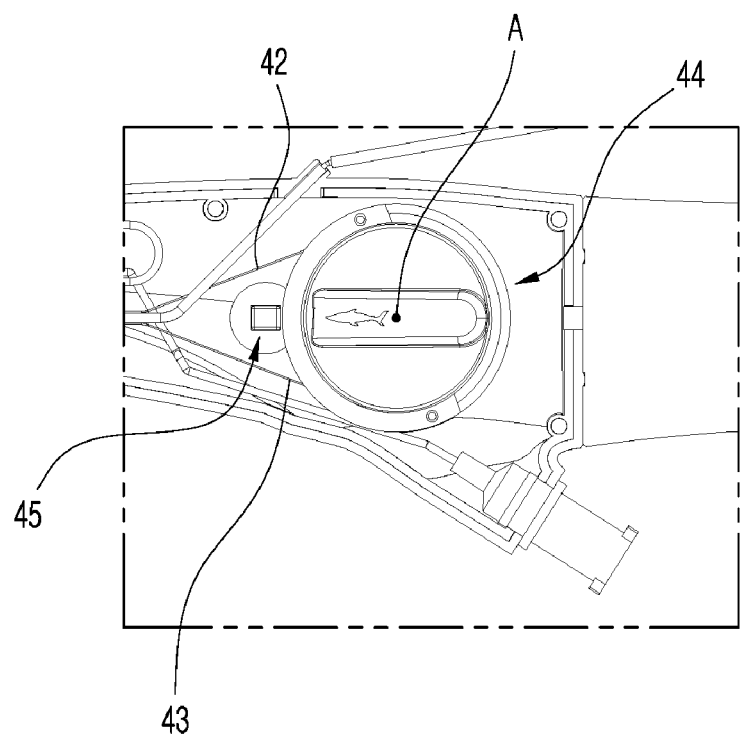
FIG. 4 is an enlarged view of a steering handle portion in FIG. 3.

As shown in FIG. 4, the steering handle 44 is rotatable clockwise or counterclockwise with respect to its central portion (central axis) A. Here, the central portion A of the steering handle 44 lies on an extension line from a center line C1 of the balloon guide tube 1, as shown in FIG. 3.

Figure 5A:
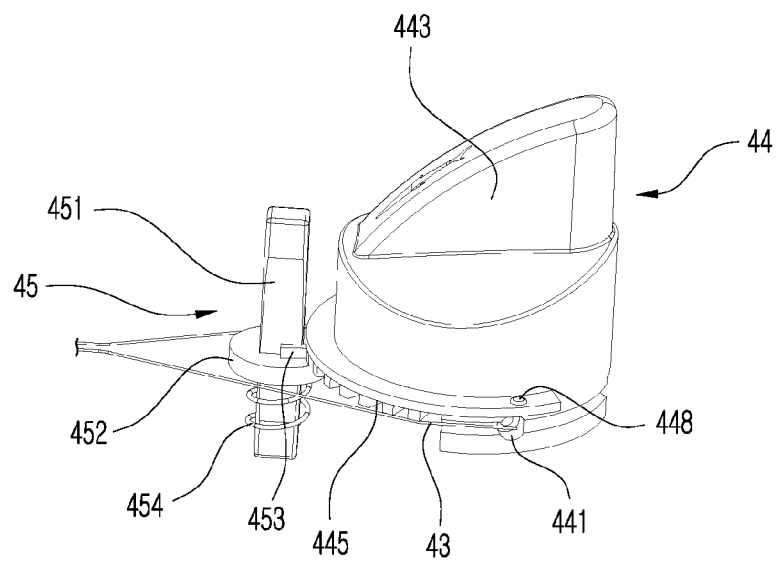
FIGS. 5A and 5B show a coupling relationship between a steering handle and a rotation stopper in the balloon catheter of FIGS. 1A to 1C.
Figure 5B:
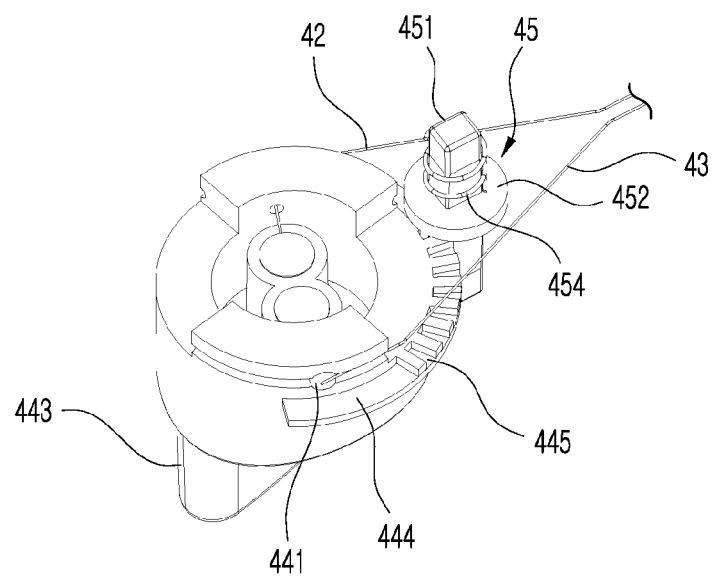
Figure 10:
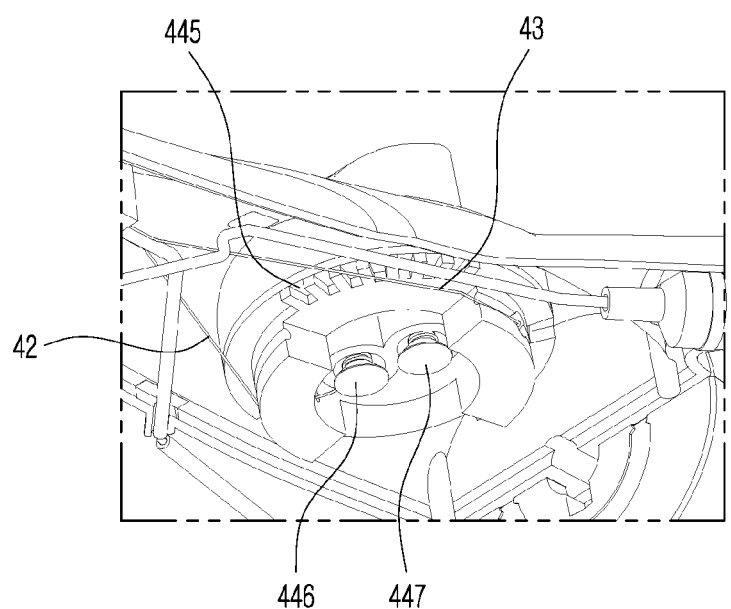
FIG. 10 is a view of the steering handle of the balloon catheter of FIGS. 1A to 1C when viewed from below.
Figure 11:
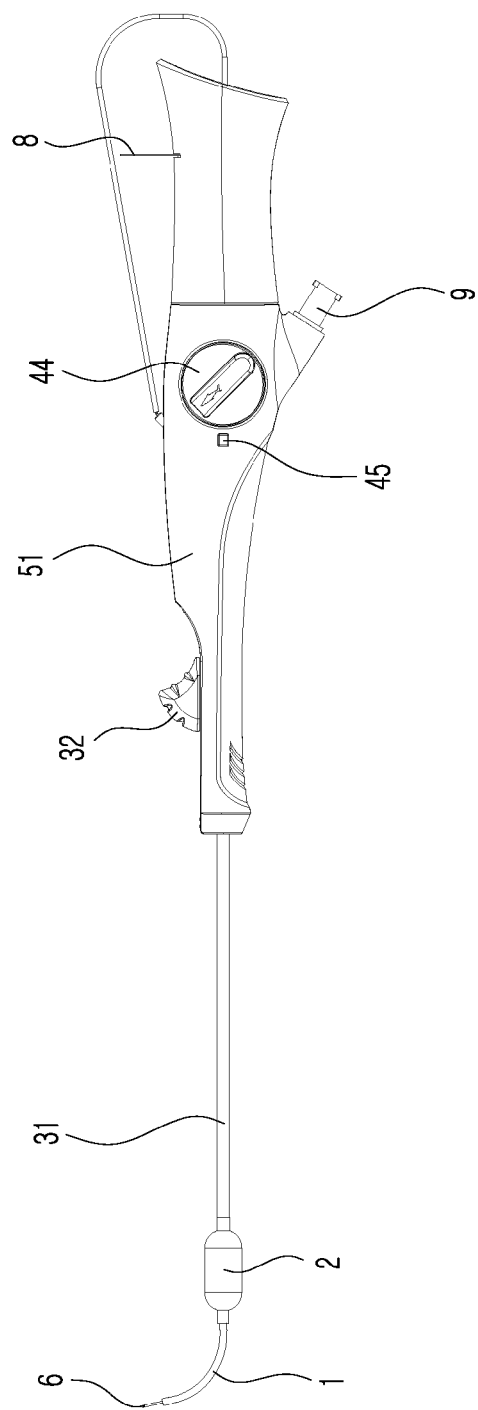
FIG. 11 shows the balloon catheter of FIGS. 1A to 1C in which an end of a balloon guide tube is bent due to a rotation of the steering handle.

As shown in FIGS. 5A and 5B, the other ends of the first and second wires 42, 43 are inserted into wire guide holes 441, 442 of the steering handle 44 formed at the same distance from the central portion A of the steering handle 44. In addition, as shown in FIGS. 4 and 10, fixing parts 446, 447 with the other ends of the first and second wires 42, 43 being respectively wound thereon, may be positioned on a lower surface of the steering handle 44 at a same distance from the central portion A of the steering handle 44. Specifically, the fixing parts 446 and 447 may have a bolt shape having a female screw formed therein, and in a state in which the first and second wires 42 and 43 are wound around its periphery, the fixing parts 446 and 447 may be inserted into a hole formed in a lower surface of the steering handle 44.

A plane formed by the first and second wires 42, 43 is perpendicular to the central portion A of the steering handle

44. In other words, the central axis of the steering handle 44 perpendicularly intersects a single plane formed by the first and second wires 42, 43.

Figure 12:
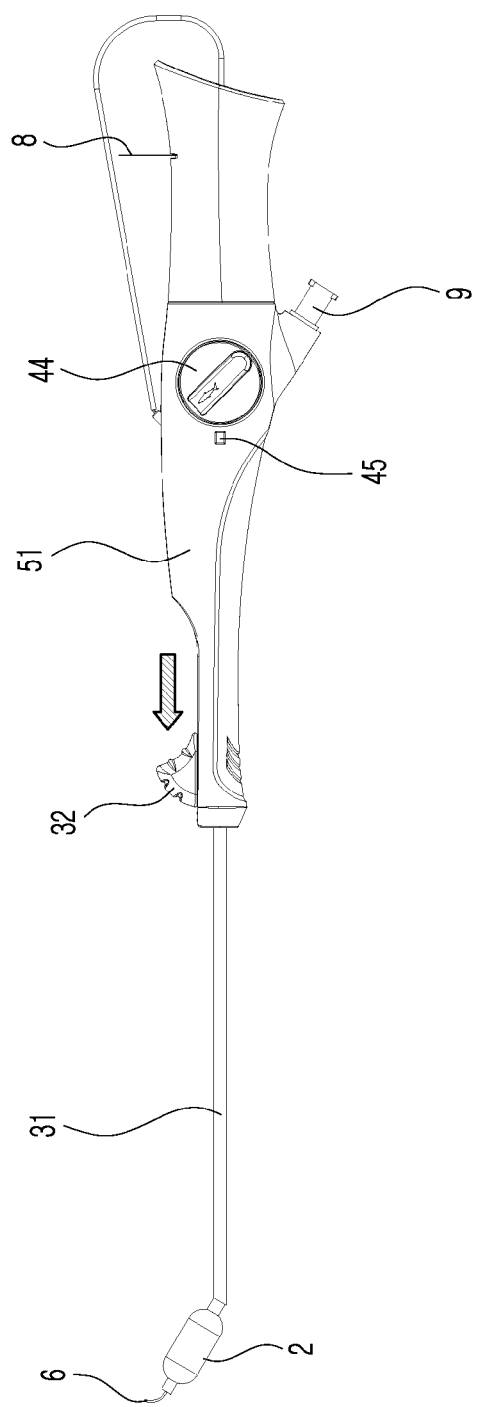
FIG. 12 shows FIG. 11 in which a tube pipe moving part is moved forward to slide the balloon along the balloon guide tube.

As a result, when the steering handle 44 is rotated to a state shown in FIG. 12 (showing the steering handle 44 having been rotated clockwise as compared to FIGS. 1A to 1C), the end of the balloon guide tube 1 is bent on the plane formed by the first and second wires 42, 43, which allows an operator to accurately and intuitively adjust the bending direction of the end of the guide tube 1. In addition, the central portion A of the steering handle 44 is positioned on an extension line from the center line C1 of the balloon guide tube 1, which allows the operator to easily adjust the degree of bending of the end of the balloon guide tube 1.

Figure 6A:
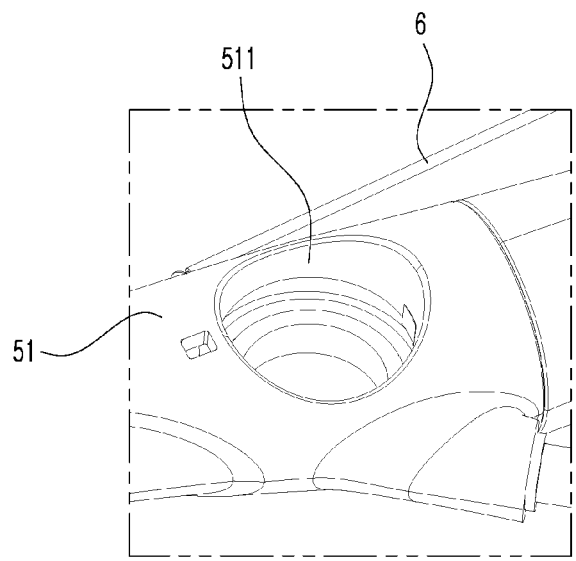
FIGS. 6A and 6B are main configuration views of the balloon catheter of FIGS. 1A to 1C showing the upper cover with the steering handle mounted thereon when viewed from above and below.
Figure 6B:
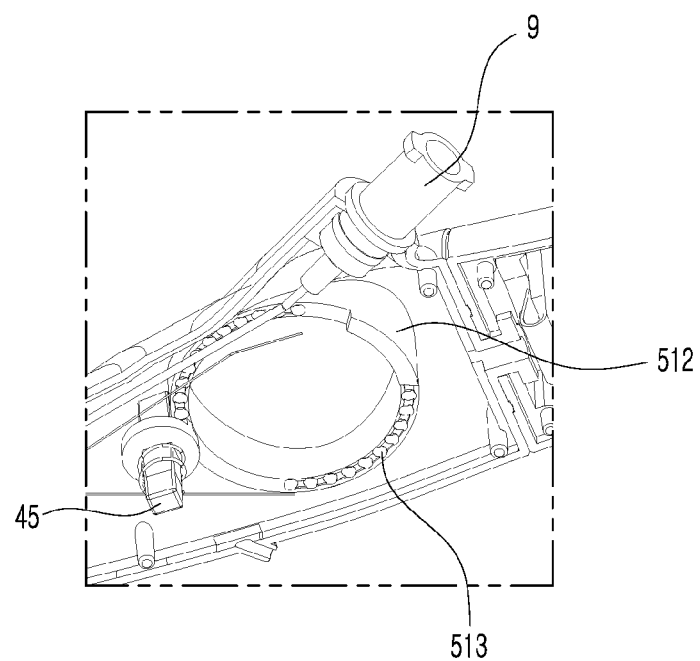

As shown in FIGS. 6A and 6B, the upper cover 51 of the body portion 5 includes a steering handle through hole 511 through which a steering handle body 443 of the steering handle 44 is protruded, and a wall portion 512 extending from a periphery of the steering handle through hole 511 into the interior of the upper cover 51.

A flange 444 of the steering handle 44 is caught by the wall portion 512 of the upper cover 51 so that the steering handle 44 is not separated from the upper cover 51. In addition, an inner space is formed when the upper cover 51 and the lower cover 52 are coupled, and this inner space is preferably formed so as to minimize the vertical clearance of the steering handle 44.

Further, as shown in FIGS. 5A and 5B, a protrusion 448 is provided on the flange 444 of the steering handle 44. As shown in FIGS. 6A and 6B, when the steering handle 44 is rotated, the protrusion 448 is sequentially inserted into and separated from a plurality of grooves 513 formed on a bottom surface of the wall portion 512 of the upper cover 51, thus allowing the operator to physically estimate the angle of rotation of the steering handle 44. To this end, the plurality of grooves 513 may be formed at a predetermined angle, for example, at intervals of 7 to 8° from each other.

As shown in FIGS. 5A and 5B, a rotation stopper 45 restricts the steering handle 44 from rotating. To this end, the rotation stopper 45 includes a bar 451 passed through the upper cover 51 and the lower cover 52, a bar flange portion 452 extending from the bar 451, a locking jaw 453 extending from the bar flange portion 452 and selectively engaged with the plurality of locking grooves 445 of the steering handle 44, and an elastic member such as a spring 454 for example, which has one end in contact with the bar flange portion 452 and the other end in contact with an inner wall of the lower cover 52.

Specifically, a plurality of locking grooves 445 are formed on a lower portion of the flange 444 of the steering handle, in a circumferential direction of the flange 444.

Figure 9:
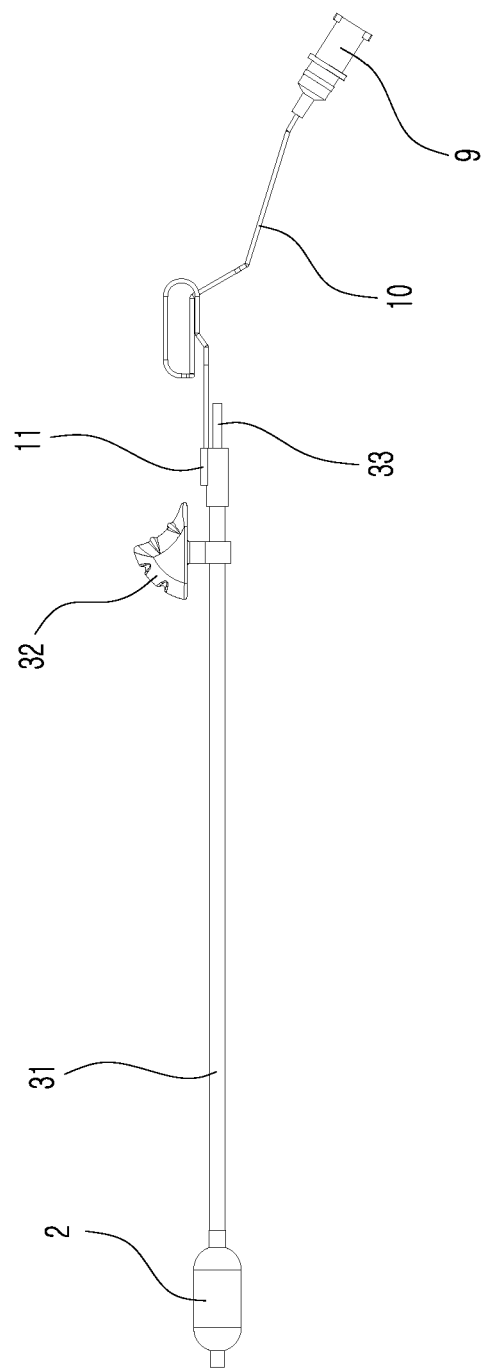
FIG. 9 is a view of the catheter of FIGS. 1A to 1C, showing components involved in the flow of fluid for balloon inflation.

As shown in FIGS. 2 and 9, the balloon moving part 3 includes a tube pipe 31 and a tube pipe moving part 32. In addition, the balloon moving part 3 is interlocked and moved integrally with the tube pipe 31 and the fluid supply tube fixing pipe 11. To this end, as shown in FIG. 1C, the body portion 5 includes a longitudinal groove 53 formed in a longitudinal direction of the body portion 5.

The tube pipe 31, with the balloon guide tube 1 enclosed therein, is slid relatively along the balloon guide tube 1, and has an inflatable balloon 2 fixed at one end.

The tube pipe moving part 32 is fixed to the tube pipe 31 and moves the tube pipe 31 forward and backward along the balloon guide tube 1.

In this example, the tube pipe 31 is coated with the same material as the balloon 2, and the balloon 2 is fused to the tube pipe 31. For example, the tube pipe 31 may be formed of a stainless steel. In the related art, the balloon 2 is fused directly to this tube pipe 31, but since the heterogeneous materials are fused to each other, this often causes incomplete fusing of the tube pipe and the balloon, resulting in leakage of the fluid out of the balloon when the balloon is inflated upon inflow of the fluid. In this embodiment, the above problem is prevented by first coating an outer surface of the tube pipe 31 with the same material as the balloon 2, and then fusing the balloon 2 to the tube pipe 31. For reference, a reflow process may be applied as an example, to coat the same material as the balloon on the outer surface of the tube pipe 31.

Figure 7:
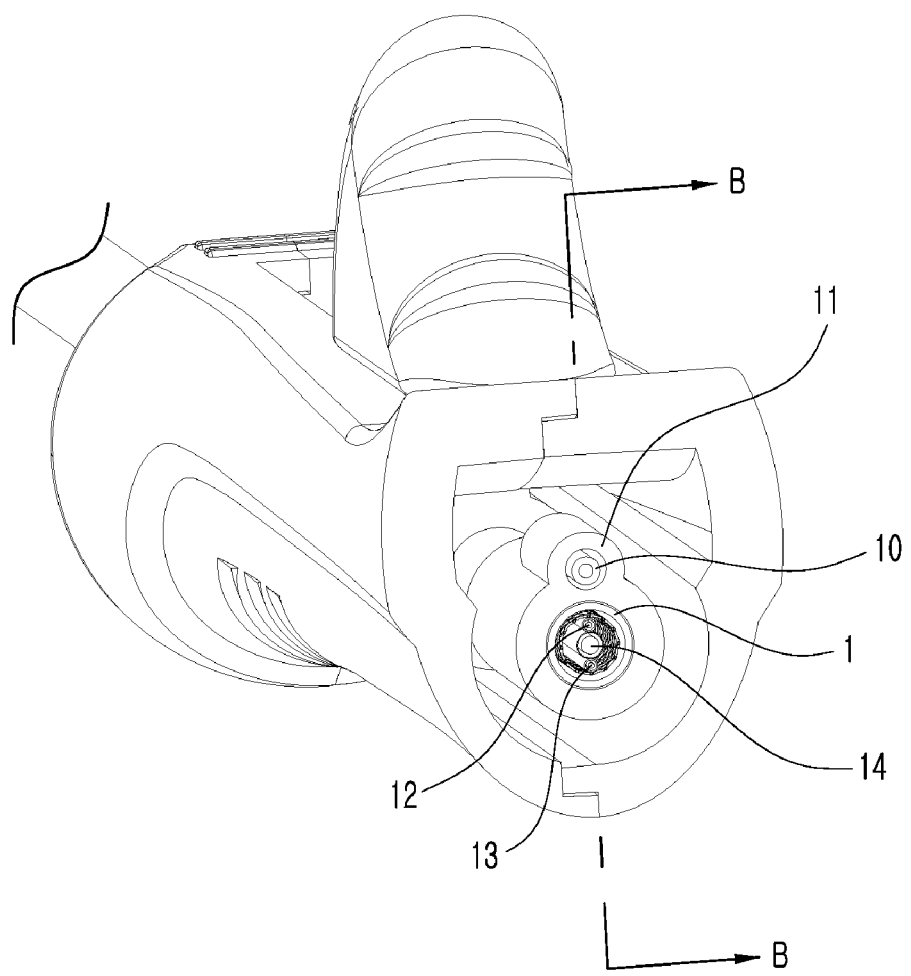
FIG. 7 is a cross-sectional view taken along the line A-A in FIG. 3.

As shown in FIG. 7, three through holes 12, 13, 14 may be formed in the balloon guide tube 1. The first and second wires 42, 43 may be passed through two 12 and 13 of these through holes, respectively, and a LED fiber 6 may be passed through the other through hole 14 that is positioned in the center of the balloon guide tube 1.

As shown in FIG. 2, the body portion 5 may include a power supply such as a battery 7 for supplying power to the LED fiber 6.

In addition, the upper cover 51 may include a slit 511 formed therein, and a blocking plate 8 inserted into this slit 511 to selectively block power supply from the power supply 7 to the LED fiber 6.

Meanwhile, the balloon catheter according to the embodiment includes a fluid port 9 capable of supplying fluid to the inflatable balloon 2.

Figure 8:
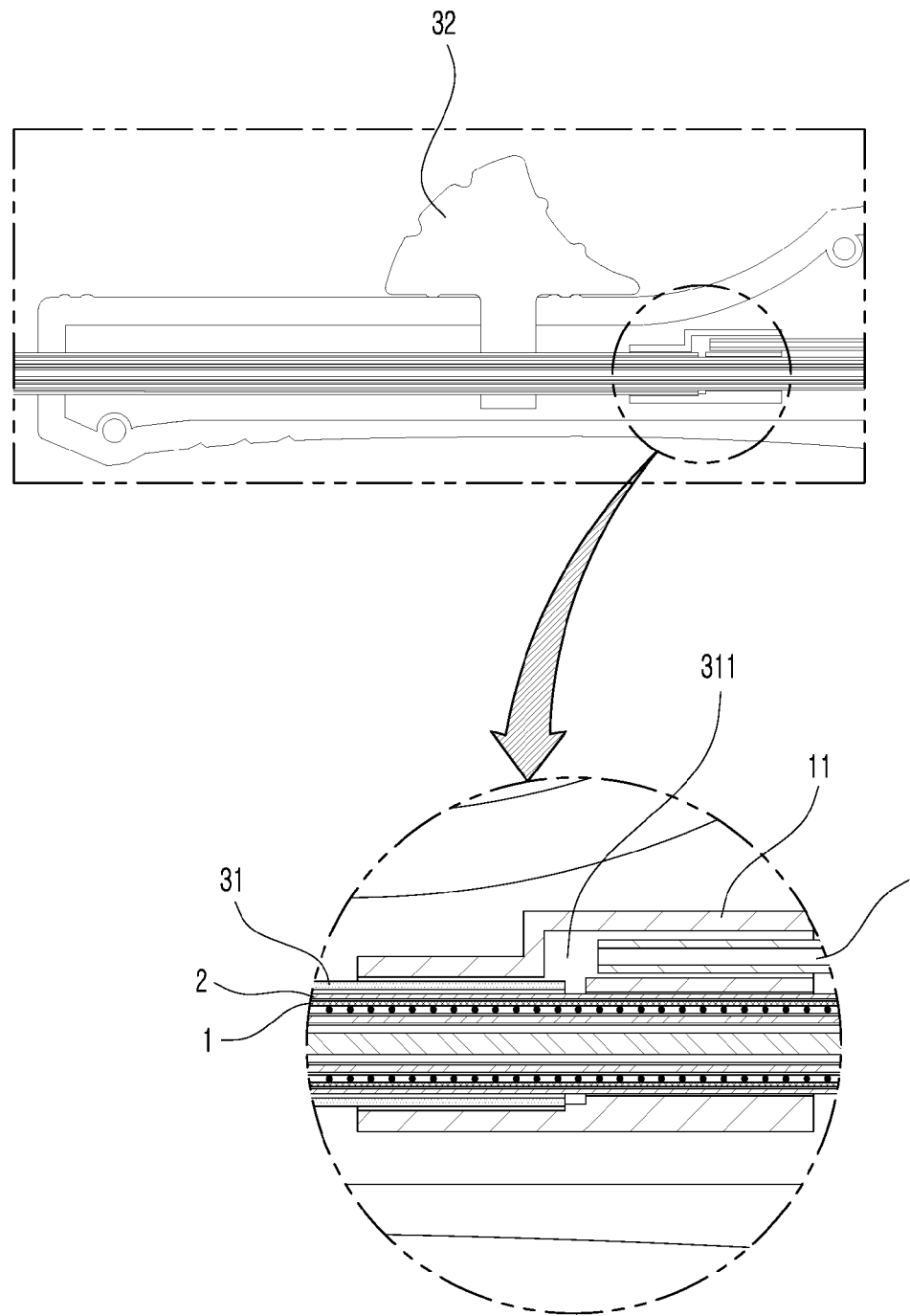
FIG. 8 is a cross-sectional view taken along the line B-B in FIG. 7.

As shown in FIGS. 8 and 9, a fluid supply tube 10 extending from the fluid port 9 is connected to a fluid supply tube fixing pipe 11 fixed to an outer wall of the tube pipe 31 while surrounding the tube pipe 31.

In addition, the tube pipe 31 includes a fluid inflow hole 311 formed in its outer wall, through which the fluid discharged from the fluid supply tube 10 is introduced.

Through this, the fluid is sequentially introduced into the fluid port 9, the fluid supply tube 10, the fluid supply tube fixing pipe 11, and the fluid inflow hole 311, and supplied to the balloon 2 through a flow path between the inner wall of the tube pipe 31 and a second tube pipe 33 surrounding the balloon guide tube 1.

Hereinafter, the operation of the balloon catheter according to an embodiment of the present disclosure having the configuration described above will be described. The balloon catheter may be used for sinusitis surgery, for example.

First, in a state as shown in FIGS. 1A to 1C, the balloon catheter is inserted into the nose for treatment of the frontal sinus, maxillary sinus, ethmoid sinus, and the like that form the sinuses.

Next, when necessary, the steering handle 44 is rotated to cause the end of the balloon guide tube 1 to bend so that the end of the balloon guide tube 1 is positioned at a desired position in the sinus. To this end, the bar 451 is pressed in a direction from the upper cover 51 toward the lower cover 52 so that the locking jaw 453 is disengaged from the locking groove 445, thereby enabling the steering handle 44 to rotate. Meanwhile, the plane formed by the first and second wires 42, 43 is perpendicular to the central portion (center axis) A of the steering handle 44, and the central portion A of the steering handle 44 is positioned on the extension line from the center line C1 of the balloon guide tube 1, so that the operator is able to accurately adjust the direction and degree of bending the end of the guide tube 1.

Then, the blocking plate 8 is separated from the slit 511 of the upper cover 51 to allow the power to be supplied to the LED fiber 6, thereby enabling visual observation on whether the balloon guide tube 1 is inserted at the desired position in the sinus.

In addition, when the steering handle 44 is rotated, the protrusion 448 of the steering handle 44 is sequentially inserted into and separated from the groove portions 513 of the upper cover 51, which allows the operator to physically estimate the angle of rotation of the steering handle 44.

Next, as shown in FIG. 12, in a state in which the end of the balloon guide tube 1 is bent so that the end of the balloon guide tube 1 is positioned at the desired position, upon removal of the force applied to the bar 451, the bar 451 is moved from the lower cover 52 toward the upper cover 51 by the restoring force of the elastic member 454 and the locking jaw 453 is engaged with the locking groove 445 to thus fix the steering handle 44 in the rotated state. Through this, the end of the balloon guide tube 1 is fixed in the bent state.

Figure 13:
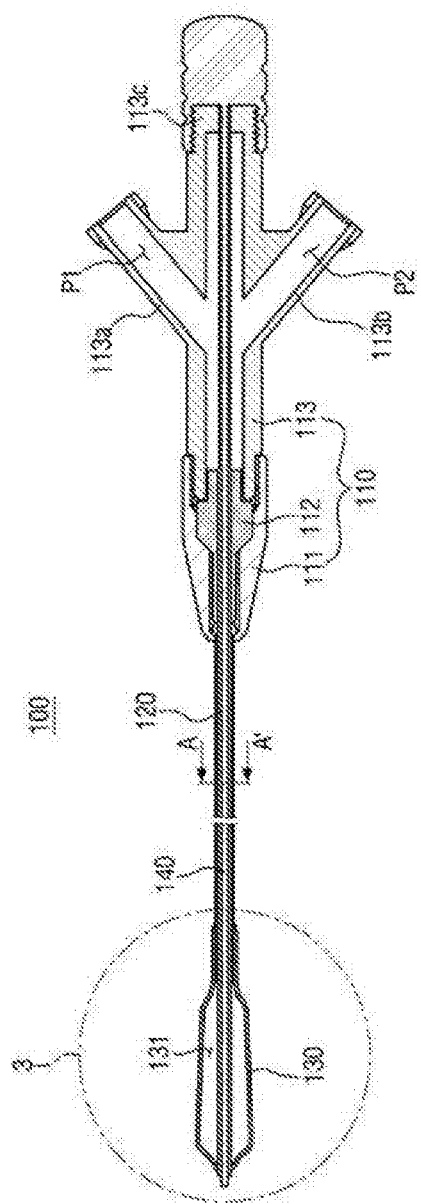
FIG. 13 shows a related balloon catheter.

Next, as shown in FIG. 13, in response to the tube pipe moving part 32 being pushed forward, the tube pipe 31 interlocked therewith is also moved forward, and at this time, the balloon 2 is slid along the balloon guide tube 1 and moved to the end of the balloon guide tube 1.

Next, when the fluid is injected into the fluid port 9, the fluid is supplied to the balloon 2 through the fluid supply tube 10, the fluid inflow hole 311, and the flow path between the inner wall of the tube pipe 231 and the outer wall of the second tube pipe 33 tube surrounding the balloon guide tube 1, so that the balloon 2 is inflated.

The present disclosure has been described in detail. However, it should be understood that the detailed description and specific examples, while indicating preferred embodiments of the disclosure, are given by way of illustration only, since various changes and modifications within the scope of the disclosure will become apparent to those skilled in the art from this detailed description.

What is claimed is:

1. A balloon catheter, comprising:
   a body portion comprising an upper cover and a lower cover;
   a balloon guide tube;
   a balloon moving part for slidably moving a balloon along the balloon guide tube; and
   a bending adjustment part for bending an end of the balloon guide tube, wherein the bending adjustment part comprises:
      a ring part fixedly enclosed in the end of the balloon guide tube;
      first and second wires each having one end fixed to the ring part; and
      a steering handle to which other ends of the first and second wires are fixed, wherein
   the steering handle is rotatable clockwise or counterclockwise with respect to a central portion of the steering handle,
   the central portion of the steering handle is positioned on an extension line from a center line of the balloon guide tube,
   the other ends of the first and second wires are respectively inserted into wire guide holes of the steering handle formed at a same distance from the central portion of the steering handle, and
   a plane formed by the first and second wires is perpendicular to the central portion of the steering handle, and
   wherein the upper cover comprises:
      a steering handle through hole through which a steering handle body of the steering handle is protruded; and
      a wall portion extending from a periphery of the steering handle through hole to an interior of the upper cover, wherein
      a flange of the steering handle is caught by the wall portion so that the steering handle is not separated from the upper cover.

2. The balloon catheter according to claim 1, further comprising:
   a rotation stopper for stopping a rotation of the steering handle, wherein the rotation stopper comprises:
      a bar passed through the upper cover and the lower cover;
      a bar flange portion extending from the bar;
      a locking jaw extending from the bar flange portion and selectively engaged with a plurality of locking grooves of the steering handle; and
      an elastic member of which one end is in contact with the bar flange portion and another end is in contact with an inner wall of the lower cover.

3. The balloon catheter according to claim 2, wherein the balloon moving part comprises:
   a tube pipe enclosing the balloon guide tube therein and relatively slidable along the balloon guide tube, and having the balloon fixed at one end; and
   a tube pipe moving part fixed to the tube pipe and moving the tube pipe in a direction in which the balloon guide tube is extended and in a direction opposite to the direction in which the balloon guide tube is extended.

4. The balloon catheter according to claim 3, wherein the tube pipe is coated with a same material as a material that the balloon is made from, and the balloon is fused to the tube pipe.

5. The balloon catheter according to claim 3, comprising a fluid port capable of supplying fluid to the balloon, wherein
   a fluid supply tube extending from the fluid port surrounds the tube pipe and is connected to a fluid supply tube fixing pipe fixed to an outer wall of the tube pipe,
   a fluid inflow hole is formed in the outer wall of the tube pipe, through which the fluid discharged from the fluid supply tube is introduced, and
   the fluid is sequentially introduced into the fluid port, the fluid supply tube, and the fluid inflow hole, and is supplied to the balloon through a flow path between an inner wall of the tube pipe and an outer wall of the balloon guide tube.

6. The balloon catheter according to claim 5, wherein the balloon moving part is interlocked and moved integrally with the tube pipe and the fluid supply tube fixing pipe.

7. The balloon catheter according to claim 1, wherein the balloon guide tube comprises three through holes formed therein,
   the first and second wires are passed through two of the three through holes, respectively, and
   an LED fiber is passed through another through hole that is positioned at a center of the balloon guide tube.

8. The balloon catheter according to claim 1, wherein, on a lower surface of the steering handle, fixing parts are positioned at a same distance from the central portion of the steering handle, and the other ends of the first and second wires are respectively wound around the fixing parts.

9. The balloon catheter according to claim 8, comprising a protrusion provided on a flange of the steering handle, wherein the protrusion is sequentially inserted into and separated from a plurality of grooves formed on a bottom surface of the wall portion of the upper cover when the steering handle is rotated.

10. A balloon catheter, comprising:

a body portion comprising an upper cover and a lower cover;

a balloon guide tube;

a balloon moving part for slidably moving a balloon along the balloon guide tube; and a bending adjustment part for bending an end of the balloon guide tube, wherein the bending adjustment part comprises:

a ring part fixedly enclosed in the end of the balloon guide tube;

first and second wires each having one end fixed to the ring part; and a steering handle to which other ends of the first and second wires are fixed, wherein the steering handle is rotatable clockwise or counterclockwise with respect to a central portion of the steering handle, the central portion of the steering handle is positioned on an extension line from a center line of the balloon guide tube, the other ends of the first and second wires are respectively inserted into wire guide holes of the steering handle formed at a same distance from the central portion of the steering handle, and a plane formed by the first and second wires is perpendicular to the central portion of the steering handle, wherein the balloon guide tube comprises three through holes formed therein, the first and second wires are passed through two of the three through holes, respectively, an LED fiber is passed through another through hole that is positioned at a center of the balloon guide tube, and wherein the body portion includes a power supply that supplies power to the LED fiber, and a blocking plate that is inserted into a slit of the upper cover.

* * * * *